(12) United States Patent
Aleckner et al.

(10) Patent No.: US 10,791,912 B2
(45) Date of Patent: Oct. 6, 2020

(54) LARYNGOSCOPE AND ADAPTIVE BLADE FOR A LARYNGOSCOPE

(71) Applicant: Karl Storz SE & Co. KG, Tuttlingen (DE)

(72) Inventors: Martina Aleckner, Tuttlingen (DE); Andreas Efinger, Tuttlingen (DE); Ralf Staud, Tuttlingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 240 days.

(21) Appl. No.: 15/886,292

(22) Filed: Feb. 1, 2018

(65) Prior Publication Data

US 2018/0235447 A1 Aug. 23, 2018

(30) Foreign Application Priority Data

Feb. 2, 2017 (DE) .................. 10 2017 102 089

(51) Int. Cl.
*A61B 1/00* (2006.01)
*A61B 1/267* (2006.01)
*A61B 1/005* (2006.01)

(52) U.S. Cl.
CPC ........ *A61B 1/00128* (2013.01); *A61B 1/0055* (2013.01); *A61B 1/267* (2013.01)

(58) Field of Classification Search
CPC .................................. A61B 1/00; A61B 1/267
See application file for complete search history.

(56) References Cited

U.S. PATENT DOCUMENTS

| | | | |
|---|---|---|---|
| 9,050,047 B2 * | 6/2015 | Chen | A61B 1/267 |
| 10,045,688 B1 * | 8/2018 | Hillman | A61B 1/0014 |
| 2018/0020906 A1 * | 1/2018 | Nettelroth | A61B 1/00105 600/190 |

FOREIGN PATENT DOCUMENTS

| | | |
|---|---|---|
| CN | 106236001 A | 12/2016 |
| DE | 69632312 T2 | 5/2005 |
| DE | 10351155 A1 | 6/2005 |
| DE | 102007026721 A1 | 5/2008 |
| EP | 1040999 A2 | 10/2000 |

(Continued)

OTHER PUBLICATIONS

European Search Report Application No. EP 18 15 4849 Completed: Jun. 5, 2018 5 pages.
German Office Action Application No. 10 2017 102 089.6 dated Dec. 1, 2017 10 pages.

*Primary Examiner* — Christopher J Beccia
(74) *Attorney, Agent, or Firm* — McGlew and Tuttle, P.C.

(57) ABSTRACT

An adaptive blade for a laryngoscope includes a proximal end, which is mechanically connectable or connected to a handle in order to form an adaptive laryngoscope, a first flexible bar, which extends from the proximal end of the adaptive blade to the distal end thereof, a second flexible bar, which extends from the proximal end of the adaptive blade to the distal end thereof, and a connecting structure with a first end, which is connected to the first flexible bar in an articulated manner, and with a second end, which is connected to the second flexible bar in an articulated manner. The first flexible bar is formed by a first member made of a first material and a second member made of a second material. An interface between the first member and the second member extends over at least half the distance between the proximal end and the distal end of the adaptive blade.

18 Claims, 4 Drawing Sheets

(56) References Cited

FOREIGN PATENT DOCUMENTS

| EP | 2241403 A1 | 10/2010 | |
|---|---|---|---|
| EP | 3266366 A1 | 1/2018 | |
| EP | 3272271 A1 | 1/2018 | |
| WO | 9730626 A1 | 8/1997 | |
| WO | 2016074894 A2 | 5/2016 | |
| WO | WO-2016074894 A2 * | 5/2016 | ........... A61B 1/0056 |

* cited by examiner

LARYNGOSCOPE AND ADAPTIVE BLADE FOR A LARYNGOSCOPE

TECHNICAL FIELD

The present invention relates to an adaptive laryngoscope, in particular an adaptive intubation laryngoscope, or an adaptive laryngoscope for surgery of the larynx or for other purposes in otorhinolaryngology, and also to an adaptive blade for such a laryngoscope.

BACKGROUND

To perform endotracheal intubation in anesthesia, emergency medicine and intensive care and to perform surgery of the larynx, an unobstructed access to the larynx, the vocal cords and, ultimately, the trachea is needed for the intubation or the surgical procedures. In these cases, a laryngoscope is used to push the tongue forward or in the rostral direction. A laryngoscope generally comprises a blade of greater or lesser curvature, at the proximal end of which blade a handle is arranged approximately at a right angle.

To facilitate adaptation to the anatomy of the patient, the blade is generally exchangeable. An intubation kit includes a large number of blades of different length and different curvature. Moreover, different designs of blade are available for different uses and/or to meet different preferences of the medical personnel, for example blades after Macintosh, Miller, Dörges and McCoy, the latter with a movable distal end.

A laryngoscope with a deformable distal end is also described in WO 97/30626. The blade 4 of the laryngoscope has several slits 40 in a central portion 14. The slits 40 divide the central portion 14 into segments 42, which are connected to each other only by narrow webs that act as flexure bearings.

EP 1 040 999 A2 describes a member for taking up forces, in which struts 11, 11a connect opposite regions of an outer skin 12, 12a to each other.

EP 2 241 403 A1 describes a manipulator tool with two flexible cheeks 8, 10. At the distal end 6 of the manipulator tool 1, the cheeks 8, 10 are connected to each other directly and also by several hinge elements 20.

DE 10 2007 026 721 A1 describes a medical gripping tool for holding body parts. The medical gripping tool 1 comprises several branches 1, each with two opposite cheeks between which connecting elements extend.

CN 106236001 A discloses a flexible laryngoscope which appears to have two bars 10, 20. A camera channel 50 is arranged on one bar 20, which camera channel 50 can be made of a transparent material or can be integrated in the bar 20 (paragraph [0025]; figures).

DE 103 51 155 A1 describes a laryngoscope for intubation. The laryngoscope comprises a blade 1, a light source 5, a cameras 6 and a screen 8.

DE 696 32 312 T2 describes a cover for a laryngoscope. The cover can be removed from the laryngoscope after use and disposed of (paragraph [0010]).

SUMMARY

It is an object of the present invention to make available an improved adaptive blade for a laryngoscope.

This object is achieved by the subject matter of the independent claims.

Developments are set forth in the dependent claims.

An adaptive blade for a laryngoscope comprises a proximal end, which is mechanically connectable or connected to a handle in order to form an adaptive laryngoscope, a first flexible bar, which extends from the proximal end of the adaptive blade to the distal end thereof, a second flexible bar, which extends from the proximal end of the adaptive blade to the distal end thereof, and a connecting structure with a first end, which is connected to the first flexible bar in an articulated manner, and with a second end, which is connected to the second flexible bar in an articulated manner, wherein the first flexible bar is formed by a first member made of a first material and a second member made of a second material, wherein an interface between the first member and the second member extends over at least half the distance between the proximal end and the distal end of the adaptive blade.

The adaptive blade is provided and designed in particular as part of a laryngoscope or in order to form a laryngoscope which is usable for intubation or for microsurgery of the larynx or for other purposes in otorhinolaryngology. The proximal end of the adaptive blade can be mechanically connected to a handle in a permanent manner, in particular for the full expected lifetime of the laryngoscope, so as not to be separable without destruction. In particular, the adaptive blade can be formed completely or partially in one piece with the handle, for example as a simultaneously produced and monolithic molding made of plastic, metal or another sufficiently elastic material. Alternatively, a coupling structure (for example in the form of a bayonet connection, a screw connection or a latch connection) can be provided at the proximal end of the adaptive blade for the purpose of coupling the latter to a handle in such a way as to be releasable therefrom without destruction, either once or repeatedly.

The first flexible bar, the second flexible bar and the connecting structures are different regions of the adaptive blade that assume different roles and functions and have different properties. The regions of the adaptive blade that form the first flexible bar, the second flexible bar and the connecting structures adjoin each other and transition into each other. Apart from the small transition regions between the first flexible bar, the second flexible bar and the connecting structures, for example the aforementioned flexure bearings, it is the case that the first flexible bar, the second flexible bar and the connecting structures are regions of the blade that can be clearly differentiated from each other.

Particularly under the forces that occur during the intended use, each of the two flexible bars is only slightly elastically or plastically deformable, if at all, in the longitudinal direction. The elastic or plastic deformability of the flexible bars in the longitudinal direction is in particular so low that a curvature of the adaptive blade, brought about by a relative displacement of proximal ends of the flexible bars or by external forces acting on the adaptive blade, is reduced by not more than 50% or by not more than 20% or by not more than 10% or by not more than 5% or by not more than 2% or by not more than 1% compared to bars that are ideally completely inelastic in the longitudinal direction.

The flexible bars are each elastically and/or plastically bendable to any appreciable extent in particular only in one direction, and they are each substantially flexurally stiff in a direction orthogonal thereto. A flexibility in a first direction or a first plane and a flexural stiffness in a second direction or second plane orthogonal thereto and a low deformability in the longitudinal direction can be achieved, for example, by a flat cross section of a bar, which has a substantially smaller extent in the first direction than in the second direction. The two flexible bars are each made in particular from a polymer, another plastic or a metal.

The first flexible bar is in particular provided and arranged to rest on a patient's tongue during the intended use. For this purpose, the first flexible bar is in particular broad and flat and has a smooth surface provided to rest on the tongue. Instead of a single second flexible bar, it is possible to provide two or more flexible second bars, in particular arranged parallel or substantially parallel to each other.

A space between two second flexible bars can be used for the insertion of a tube, an endoscope and/or another medical instrument. For this purpose, a guide channel with an open or closed cross section can be provided. This guide channel can be rigidly connected to the first flexible bar or to the second flexible bar or to one or more of several second flexible bars, particularly formed in one piece therewith.

Moreover, a light source, for example a light-emitting diode, or a fiber optic cable for transmission of illumination light, a camera or an image sensor with imaging optics or a flexible endoscope can be connectable or permanently connected to one of the flexible bars, in particular at or near the distal end thereof.

A connection is permanent if it is designed to exist for a period of time covering several medical interventions or for the full expected lifetime of the laryngoscope.

At the distal end of the adaptive blade, the distal ends of the flexible bars are connected to each other in particular in a mechanically rigid or articulated manner. In the case of an articulated connection of the flexible bars at the distal end of the adaptive blade, the distal ends of the flexible bars are mechanically connected to each other in particular in such a way that the distal ends of the flexible bars are not movable relative to each other in a direction parallel to the first flexible bar or in a direction parallel to the second flexible bar.

The first end of the connecting structure is in particular connected in an articulated manner to the first flexible bar by a first flexure bearing. The second end of the connecting structure is in particular connected to the second flexible bar by a second flexure bearing between its ends, the connecting structure is in particular flexurally stiff or at least much less elastic than the flexure bearings at the ends of the connecting structure, such that a deformation of the connecting structure is largely or completely limited to the flexure bearings.

The adaptive blade can have several identical or similar connecting structures (distinguished in particular mainly by different lengths), wherein each connecting structure connects the first flexible bar and the second flexible bar to each other. If the first flexible bar and the second flexible bar are connected to each other by several connecting structures, the length of the connecting structures decreases in particular from the proximal end to the distal end. If the adaptive blade has several second flexible bars, every second flexible bar is in particular connected to the first flexible bar by one or more connecting structures.

In particular, the first member is formed by a first body made of a first material, and the second member is formed by a second body made of a second material.

The first flexible bar, the second flexible bar and the connecting structures can be formed at least partially from the same materials. In particular, both the first flexible bar and the second flexible bar are each formed from two different materials, namely from the first material of the first member (or first body) and the second material of the second member (or second body). For example, a first region of the first member can form a first subregion of the first flexible bar and a second region of the first member can form a first subregion of the second flexible member, wherein a first region of the second member from the second material forms a second subregion of the first flexible bar, a second region of the second member forms a second region of the second flexible bar, and a third region of the second member forms the connecting structure, or third regions of the second member form the connecting structures of the adaptive blade. Thus, both the first member and the second member can be included at several regions of the adaptive blade. The first member and the second member are in particular clearly distinguishable, since the first material of the first member is different than the second material of the second member. Accordingly, the interface between the first member and the second member is clearly defined.

The interface between the first member and the second member is the surface along which the first member and the second member directly adjoin each other. The interface between the first member and the second member at the same time forms at least part of the surface of the first member and part of the surface of the second member. The first member and the second member can be connected cohesively to each other at their entire interface. Alternatively or in addition, the first member and the second member can be joined in some other way.

The first member and the second member are in particular produced at different and successive steps of a production method. For example, the first member is produced first, then the second member, for example by encapsulation of the first member with the second member or by embedding the first member in the second material of the second member.

An adaptive blade with the features and properties described here can be adapted to the anatomy of a patient by medical personnel. Alternatively or in addition, during the intended use an adaptive blade with features and properties described here can completely or partially adapt automatically, by elastic and/or plastic deformation, to a patient's anatomy, in particular to the curvature, shape and/or size of the tongue or of the pharynx of the patient.

This adaptation to the patient's anatomy is facilitated in particular by the flexural elasticity of the two bars and by the connecting structure or the connecting structures. The connecting structure forms a mechanical connection of the two flexurally elastic bars, in such a way that the two flexurally elastic bars are movable relative to each other substantially in their longitudinal directions, but the distances between them are not substantially alterable. This facilitates a merely local retreat of the adaptive blade. For example, the adaptive blade can retreat at a convex region of the surface of a patient's tongue, while a distal region of the adaptive blade can however rest at a concave region of the surface of the tongue. The adaptive blade can thus apply a comparatively uniform pressure to the surface of the tongue, specifically both in concave regions and also in convex regions of the surface of the tongue.

An adaptive blade of this kind can thus be used for patients with different anatomical characteristics, and therefore the number of blades that have to be kept in stock can be significantly reduced. Moreover, time can be saved particularly in emergency medicine, since a blade does not first of all have to be selected and connected to the handle; instead, an adaptive blade already connected to a handle is adapted and/or adapts during its use to the anatomy of the patient.

The formation of the first flexible bar by two members made of two different materials can facilitate an improvement of the mechanical properties of the first flexible bar. In particular, desired elastic properties of the first flexible bar can be combined with desired atraumatic properties of the surface of the first flexible bar.

In an adaptive blade as described here, the first member is in particular a core member, wherein the second member is a jacket member in which the first member is at least partially embedded.

In an adaptive blade as described here, the second member covers in particular at least a third or at least a half or at least two thirds or at least three quarters or at least nine tenths of the surface or the entire surface of the first member.

The second member can be generated by encapsulating or overmolding the first member with the material of the second member. A desired wall thickness of the second member can be ensured in particular by one or more spacers (for example rings or other insert parts) between the first member and the wall of the mold. These spacers have in particular the material from which the second member is formed.

Since the first member is at least partially embedded in the second member or the second member covers at least part of the surface of the first member, it is possible to optimize the first member for desired mechanical properties of the first flexible bar, and at the same time the second member can ensure atraumatic properties of the first flexible bar and of the adaptive blade. For example, the first member can have sharp edges and corners, but these are covered by the second member and cannot therefore come into contact with a patient.

In an adaptive blade as described here, the first material has a first elastic modulus $E_1$ and the second material has a second elastic modulus $E_2$, wherein the first elastic modulus $E_1$ is greater than the second elastic modulus $E_2$.

In particular, the first elastic modulus $E_1$ is greater than the second elastic modulus $E_2$ by at least a factor of 10. In this way, elastic properties of the first flexible bar and of the adaptive blade can be defined largely by elastic properties of the first member.

In an adaptive blade as described here, the first material is in particular a metal.

The first material is in particular spring steel 1.4310, nitinol or another shape-memory alloy or another pseudoelastic material or another alloy.

In an adaptive blade as described here, the first material comprises in particular a fiber-reinforced plastic.

In an adaptive blade as described here, the second material comprises in particular a silicone, a silicone rubber, a silicone elastomer, a silicone resin or another elastomer.

Silicone means in particular poly(organo)siloxane. A silicone resin is in particular polymethyl siloxane or polymethyl phenyl siloxane.

In an adaptive blade as described here, the first member is in particular formed from a metal sheet or from another plate-shaped semi-finished product.

In an adaptive blade as described here, the thickness of the metal sheet has in particular a value in the range of 0.1 mm to 0.4 mm or in the range of 0.2 mm to 0.3 mm.

In an adaptive blade as described here, the first member has in particular a substantially rectangular cross section whose the width is at least twenty times or at least fifty times or at least a hundred times its height.

The stated ratio between width and height of the rectangular cross section of the first member applies in particular at several locations or all locations on the first member.

In an adaptive blade as described here, the first member has in particular a recess.

The recess in the first member is in particular an opening or a through-hole, such that the first member is multiply contiguous in the mathematical sense. Alternatively, the recess only locally reduces the thickness or the cross section of the first member. The first member can have several recesses.

One or more recesses at the first member can increase its elasticity in a predetermined direction. Similarly to a large ratio between width and height of a cross section of the first member, this can facilitate a high flexural elasticity with at the same time a low torsional elasticity of the first member and therefore of the entire first flexible bar.

In an adaptive blade as described here, the recess extends in particular orthogonally or substantially orthogonally to the longitudinal direction of the first flexible bar.

The recess extends in a direction if it has the greatest linear dimension in this direction. An extent of the recess orthogonally or substantially orthogonally to the longitudinal direction of the first flexible bar can facilitate a high flexural elasticity of the first region and of the first flexible bar and at the same time a low torsional elasticity, in relation to the longitudinal direction of the first bar.

In an adaptive blade as described here, the recess has in particular a first maximum dimension in the longitudinal direction of the first flexible bar and a second maximum dimension orthogonally to the longitudinal direction of the first flexible bar, wherein the first maximum dimension is not more than a third or not more than a fifth or not more than a tenth of the second maximum dimension.

The recess is configured in particular as an oblong hole.

In an adaptive blade as described here, the first member is in particular undulating.

In particular, a longitudinal section of the first member in a plane parallel to the longitudinal direction of the first flexible bar has an undulating shape with one or more waves or corrugations. The wave or the waves or the corrugation or the corrugations in each case extend in particular over the entire width or substantially over the entire width of the first member (in particular at least two thirds or at least four fifths or at least nine tenths of the width). One or more waves or corrugations of the first member can generate desired mechanical properties of the first member, in particular a high flexural elasticity in one direction and at the same time a low torsional elasticity.

In an adaptive blade as described here, several recesses or several waves or several corrugations of the first member have in particular different dimensions and/or different spacings.

Several recesses or several waves or several corrugations of the first member can have different widths (in particular measured in the longitudinal direction of the first flexible bar) and/or different lengths (in particular measured in a direction orthogonal to the longitudinal direction of the first flexible bar). Several recesses can have different depths, several waves or corrugations can have different heights. Dimensions and/or spacings of the recesses or waves or corrugations vary in particular monotonically or strictly monotonically from the proximal end to the distal end.

For example, the dimensions of recesses or waves or corrugations decrease from the proximal end to the distal end in order for the elasticity of the first member to increase from the proximal end to the distal end. Alternatively, the dimensions of recesses or waves or corrugations can decrease from the proximal end to the distal end in order for the elasticity of the first member to decrease from the proximal end to the distal end.

Alternatively or in addition, the spacings between adjacent recesses or waves or corrugations can increase or decrease from the proximal end to the distal end in order for the elasticity of the first member to vary from the proximal end to the distal end. For example, the spacings between a large number of recesses formed as oblong holes can decrease from the distal end to the proximal end, as a result of which the width of webs between adjacent recesses also decreases from the distal end to the proximal end.

In an adaptive blade as described here, the first member in particular also forms at least part of the second flexible bar.

The second member can also form part of the second flexible bar. Moreover, the second member can partially or largely or completely cover or enclose or encase the first member in the region of the second flexible bar.

In an adaptive blade as described here, the first member is in particular formed by cutting, punching or etching from a metal sheet or from another plate-shaped semi-finished product.

The metal sheet or the other plate-shaped semi-finished product can be bent or otherwise plastically deformed before or after punching, cutting or etching. In particular, waves or corrugations may have been generated before or after cutting, punching or etching.

In an adaptive blade as described here, the first member at the distal end of the adaptive blade has in particular a curved region and merges from the first flexible bar into the second flexible bar.

The first member at the distal end of the adaptive blade can have one or two or more curved regions and, with this or these, can change its basic direction in particular by a total of at least 150 degrees or at least 160 degrees or at least 170 degrees.

The Gaussian curvature of the first member can be zero in the whole region of the distal end of the adaptive blade, including the curved region, or can deviate from zero.

In an adaptive blade as described here, a region of the first member, arranged in the second flexible bar, comprises in particular a tube and a wire partially arranged in the tube, or a wire with a cross section varying from the proximal end to the distal end, or in some other way has a cross section varying from the proximal end to the distal end.

In an adaptive blade as described here, the connecting structure is in particular formed by the second member.

The connecting structure or several connecting structures or all connecting structures of the adaptive blade can be formed exclusively by the second member. Alternatively, the connecting structure or several or all connecting structures of the adaptive blade can be formed by the first member and by the second member. Alternatively, further members can be included at the connecting structure or the connecting structures.

In an adaptive blade as described here, the first flexible bar in particular comprises a third member made from the first material or from a further material, wherein the second member is arranged between the first member and the third member.

The third member can be formed from a further material different than the first material and the second material. The first member, the second member and the third member can be arranged like a sandwich. The first member and the third member then adjoin opposite surfaces of the second member, and the first member and the third member can together cover a large part (in particular at least half, at least a quarter or at least nine tenths) of the surface of the second member.

In an adaptive blades as described here, the first member has in particular the form of a multiple perforated tube.

The first member has in particular the form of a multiple perforated cylindrical or conical tube with any desired base or any desired cross section. Base and/or cross sections of the tube are in particular circular, elliptic or rectangular, with or without corners that are rounded (i.e. that are replaced by quarter circles).

In an adaptive blade as described here, the first member has in particular the form of a section of a surface of a generalized cone.

The generalized cone has any desired base, but in particular a convex base. The base of the generalized cone is, for example, circular, elliptic, rectangular, polygonal, with or without rounded corners.

In an adaptive blade as described here, the first member has in particular a first region, which is arranged in the first flexible bar, a second region, which is arranged in the second flexible bar, and several arc-shaped regions, which connect the first region to the second region and are arranged in several connecting structures of the adaptive blade.

The first region and the second region are each in particular substantially straight webs, or webs that are curved only in one direction. The arc-shaped regions of the first member, which connect the first region to the second region, are each in particular shaped as an arc of a circle or merge or have the shape of an arc of a circle in a plane development of the first member.

In an adaptive blades as described here, two regions of the first member shaped as arcs of a circle are in particular arranged such that they intersect each other at two locations.

In an adaptive blade as described here, the first member is in particular formed from a metal sheet which has been bent to form a tube shape and has been joined along a weld seam extending in the longitudinal direction of the adaptive blade.

The metal sheet is in particular multiple perforated.

An adaptive blade for a laryngoscope comprises a proximal end which is mechanically connectable or connected to a handle in order to form an adaptive laryngoscope, a first flexible bar, which extends from the proximal end of the adaptive blade to the distal end thereof, a second flexible bar, which extends from the proximal end of the adaptive blade to the distal end thereof, and a connecting structure with a first end, which is connected to the first flexible bar in an articulated manner, and with a second end, which is connected to the second flexible bar in an articulated manner, wherein a multiple perforated tube forms the first flexible bar, the second flexible bar and the connecting structure.

The adaptive blade can have features, properties and functions similar to those of the adaptive blades described above. In particular, at the distal end of the adaptive blade, the flexible bars can be connected to each other mechanically rigidly or in an articulated manner. The ends of one or more connecting structures can each be connected to the flexible bars by flexure bearings. The multiple perforated tube can be cylindrical or conical with any desired base or any desired cross sections. The base or the cross sections of the multiple perforated tube are in particular circular, elliptic or polygonal, with or without rounded corners.

In an adaptive blade as described here, the multiple perforated tube has in particular the form of a section of a surface of a generalized cone.

The generalized cone has any desired base, but in particular a convex base. The base of the generalized cone is, for example, circular, elliptic, rectangular, polygonal, with or without rounded corners.

In an adaptive blade as described here, the multiple perforated tube has in particular a first region, which is arranged in the first flexible bar, a second region, which is arranged in the second flexible bar, and several arc-shaped regions, which connect the first region to the second region and form several connecting structures of the adaptive blade.

The arc-shaped regions of the multiple perforated tube, which connect the first region to the second region, are each in particular shaped as an arc of a circle or have the shape of an arc of a circle in a plane development of the multiple perforated tube.

In an adaptive blade as described here, two regions of the multiple perforated tube shaped as arcs of a circle are in particular arranged such that they intersect each other at two locations.

In an adaptive blade as described here, the multiple perforated tube is in particular formed from a metal sheet which has been bent to form a tube shape and has been joined along a weld seam extending in the longitudinal direction of the adaptive blade.

An adaptive blade as described here further comprises in particular an elastic cover member for protecting the adaptive blade from contamination and other environmental influences.

The elastic cover member is in particular exchangeable after each use of the adaptive blade. The elastic cover member can have an elastic film or an elastic woven fabric.

An adaptive blade as described here further comprises in particular a channel into which at least one of an endoscope, a light source and another medical instrument can be inserted.

An adaptive laryngoscope as described here can be provided and designed for repeated use and repeated sterilization (in particular steam sterilization in an autoclave) or can be provided and designed to be used just once and then disposed of.

An adaptive laryngoscope comprises an adaptive blade, as described here, and a handle, which is mechanically connectable or connected to the proximal end of the adaptive blade.

The adaptive laryngoscope is in particular an intubation laryngoscope and/or is provided for use in microsurgery of the larynx or for other applications in otorhinolaryngology.

The handle can be mechanically connectable or connected to the proximal end of the adaptive blade in such a way that the handle is releasable from the proximal end of the adaptive blade without destruction is or is not releasable therefrom without destruction.

BRIEF DESCRIPTION OF THE FIGURES

Embodiments are explained in more detail below with reference to the attached figures, in which.

DETAILED DESCRIPTION

Figure 1:
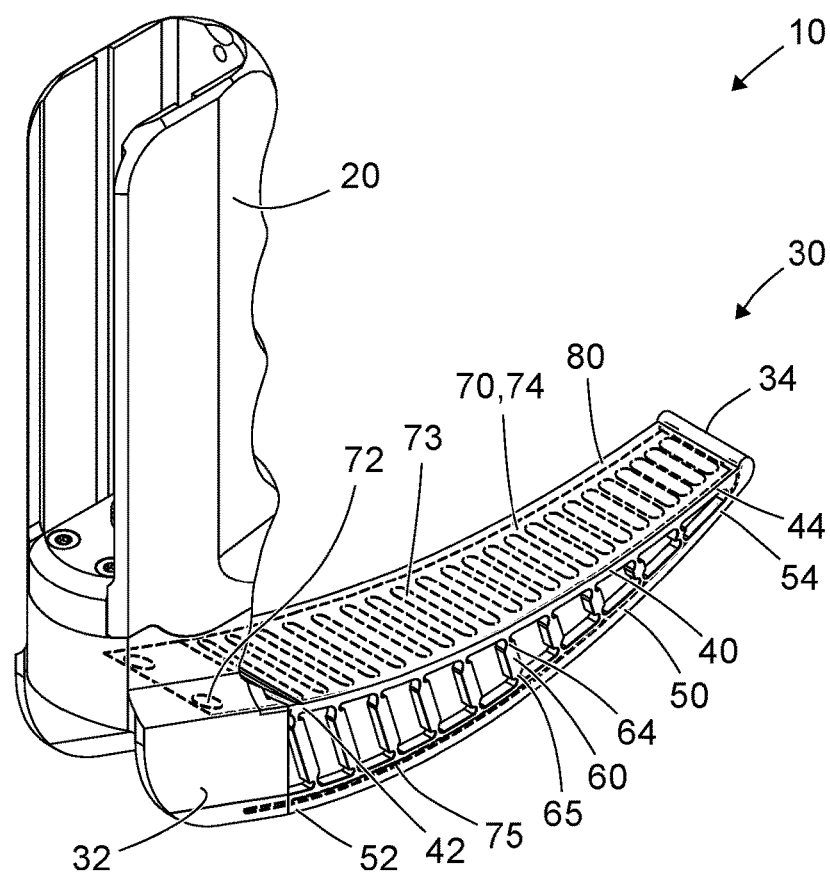
FIG. 1 shows a schematic axonometric view of an adaptive laryngoscope.

FIG. 1 shows a schematic axonometric view of an adaptive intubation laryngoscope 10 with a handle 20 for manually holding and guiding the intubation laryngoscope 10. The adaptive intubation laryngoscope 10 further comprises an adaptive blade 30 with a proximal end 32 and a distal end 34. The adaptive blade 30 is slightly curved and has a cross section that grows smaller toward the distal end 34. The proximal end 32 of the adaptive blade 30 is mechanically connected to the handle 20 in such a way that the region of the adaptive blade 30 adjoining the proximal end 32 encloses an angle of approximately 90 degrees (in the range between ca. 80 degrees and 130 degrees) with the handle 20.

In FIG. 1, the handle 20 and the adaptive blade 30 are shown mechanically connected to each other. The connection between the handle 20 and the adaptive blade 30 is effected in particular by means of a mechanical coupling (not visible in FIG. 1), which facilitates separation of the adaptive blade 30 from the handle 20 without destruction. Alternatively, the handle 20 and the adaptive blade 30 can be connected to each other permanently and are not separable without destruction.

The adaptive blade 30 has a first flexible bar 40 and two second flexible bars 50. In the view in FIG. 1, only one of the two second flexible bars 50 is fully visible, the other second flexible bar being concealed behind the first flexible bar 40.

The first flexible bar 40 has substantially a broad, flat rectangular cross section. The surface of the first flexible bar 40, visible in FIG. 1, for resting on a patient's tongue is smooth or largely smooth.

The second flexible bars 50 each have a substantially square or rectangular cross section. The distance between the second flexible bars 50 corresponds substantially to the width of the first flexible bar 40.

Near the proximal end 32 of the adaptive blade 30, the second flexible bars 50 are substantially parallel to the edges of the first flexible bar 40. Toward the distal end 34 of the adaptive blade 30, the distances of the second flexible bars 50 from the edges of the first flexible bar 40 decrease. The width of the first flexible bar 40, hence also the distance of the two second flexible bars 50 from each other, also decreases slightly toward the distal end 34 of the adaptive blade 30. At the distal end 34 of the adaptive blade 30, the distal end 44 of the first flexible bar 40 and the distal ends of the second flexible bars 50 are mechanically connected to each other rigidly.

The second flexible bars 50 are connected to the respectively opposite edges of the first flexible bar 40 by several mutually similar struts or connecting structures 60. The first end 64 of each connecting structure 60 is connected to the first bar 40. The second end 65 of each connecting structure 60 is connected to the second bar 50. Each connecting structure 60 connecting the first flexible bar 40 to one of the second flexible bars 50 is parallel or substantially parallel to a further connecting structure 60 connecting the first flexible bar 40 to the second flexible bar 50.

Each connecting structure 60 has substantially the shape of a straight rod with a substantially constant cross section between the ends 64, 65. Each connecting structure 60 has, in the transition regions of its ends 64, 65 to the first flexible bar 40 and to the second flexible bar 50, reduced cross sections and therefore a locally increased flexural elasticity. These transition regions with reduced cross sections form flexure bearings which set only slight restoring forces against a change of the angles between the connecting structures 60 and the flexible bars 40, 50.

The connecting structures 60 and the transition regions between the ends 64, 65 of the connecting structures and the flexible bars 40, 50 are dimensioned such that there is no appreciable change of the lengths of the connecting structures at the forces that occur in the intended use of the adaptive intubation laryngoscope 10. The distances of the second flexible bars 50 from the respectively opposite edges of the first flexible bar 40 are fixed or defined in a substantially unalterable manner. However, the second flexible bars 50 can be moved relative to the opposite edges of the first flexible bar 40. The relative movement of the second flexible bars 50 and of the first flexible bar 40 is orthogonal or substantially orthogonal to the connecting structures 60 and therefore, in the configuration indicated in FIG. 1, parallel or substantially parallel to the flexible bars 40, 50.

The adaptive blade 30 of the adaptive intubation laryngoscope 10 is formed substantially from a first member 70 as core member and of a second member 80 as jacket member. In the example shown, the first member 70 is completely surrounded by the second member 80. If the second member 80 is not made of a transparent material, the first member 70 is therefore not visible, and it is indicated only with broken lines in FIG. 1.

The first member 70 is arranged both in the first flexible bar 40 and also in the second flexible bars 50 and thus forms, together with the second member 80, the first flexible bar 40 and the second flexible bars 50. In the example shown, the first member 70 is not arranged in the connecting structures 60; the connecting structures 60 are thus formed exclusively by the second member 80.

In the example shown, the first member 70 is formed from a cut, punched or milled metal sheet which is bent beforehand or subsequently.

At the proximal end 32 of the adaptive blade 30, the first member 70 has two fastening holes 72. The fastening holes 72 facilitate fastening of the first member 70 to the handle 20 of the intubation laryngoscope 10 or at a coupling or connecting structure at the proximal end 32 of the adaptive blade 30, wherein the coupling or connecting structure can in turn be connected to the handle 20 permanently or releasably.

The region 74 of the first member 70 arranged in the first flexible bar is substantially web-shaped and has several recesses 73. The recesses 73 and in particular through-holes. In the example shown, each individual recess 73 is narrow and elongate with two parallel straight sides and two rounded ends. The recesses 73 are arranged parallel to each other and orthogonal to the longitudinal direction of the first flexible bar 40.

The recesses 73 influence the elasticity of the first member 70 and of the first bar 40. In particular, the recesses 73 increase the flexural elasticity of the region 74 of the first member 70 arranged in the first flexible bar 40 and thus the flexural elasticity of the first flexible bar 40. However, the recesses 73 increase the flexural elasticity of the first member 70 and of the first flexible bar 40 especially in terms of a deformation in the plane spanned by the handle 20 and the adaptive blade 30, thereby facilitating an increase or decrease of the curvature of the adaptive blade 30. By contrast, the elasticity of the first member 70 and thus of the first flexible bar 40 and thus of the entire adaptive blade 30 in terms of torsion is increased by the recesses 73 to a comparatively lesser extent. By virtue of their elongate shape and their orientation orthogonal to the longitudinal direction of the first bar 40, the recesses 73 thus improve the ratio between flexural elasticity and torsional elasticity of the adaptive blade 30.

Figure 2:
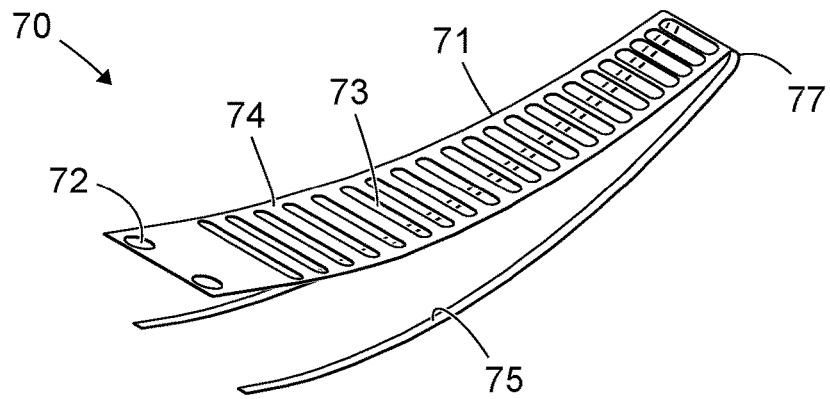
FIG. 2 shows a schematic axonometric view of a first member of an adaptive blade.

FIG. 2 shows a schematic axonometric view of the first member 70 of the adaptive blade 30 shown in FIG. 1. The viewing direction from which the first member 70 is shown in FIG. 2 corresponds to that of FIG. 1. Since the first member 70 is shown in FIG. 2 without the casing provided by the second member 80, the first member 70 is fully visible and is therefore shown in solid lines.

It will be seen in FIG. 2 that the distances between adjacent recesses 73 in the region 74 of the first member 70 provided for the first flexible bar 40 decrease from the proximal end (on the left in FIGS. 1 and 2) to the distal end (on the right in FIGS. 1 and 2). This can contribute to the adaptive blade having an elasticity that increases from the proximal end to the distal end.

In the example shown, the distances of the ends of the recesses 73 from the longitudinal edges 71 of the first member 70 decrease toward the proximal end. This too can influence the elasticity of the adaptive blade, particularly its elasticity near the proximal end.

FIG. 2 also shows both regions 75 of the first member 70 which are provided for arrangement in a respective second flexible bar 50 of the adaptive blade 30 (cf. FIG. 1). These regions 75 of the first member 70 each have the shape of a web that is curved substantially only in one direction.

In the region provided for arrangement at the distal end 34 of the adaptive blade 30 (cf. FIG. 1), the first member 70 has a curved region 77 with a small radius of curvature dictated by the dimensions of the distal end 34 of the adaptive blade 30.

Figure 3:
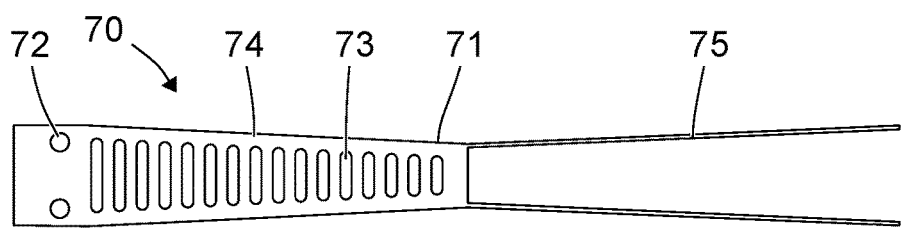
FIG. 3 shows a schematic view of a further first member of an adaptive blade.

FIG. 3 shows a schematic view of a further first member 70 which, in terms of certain features, properties and functions, is similar to the first member 70 shown in FIGS. 1 and 2. The first member 70 shown in FIG. 3 is provided, for example, for an adaptive blade and for an adaptive intubation laryngoscope, which are similar to or in other respects identical to those shown in FIG. 1.

The first member 70 is shown in FIG. 3 in an uncurved state, which is the state in which it is present, for example, directly after being cut or punched from a metal sheet.

In the first member 70 shown in FIG. 3, the lengths of the recesses 73 measured in a direction orthogonal to the longitudinal direction of the first member 70 (and therefore of the adaptive blade for which the first member 70 is provided) decrease from the proximal end to the distal end to the same extent as the width of the region 74 provided for arrangement in the first flexible bar of the adaptive blade. The distances of the ends of the recesses 73 from the longitudinal edges 71 of the first member 70 are therefore substantially constant.

Figure 4:
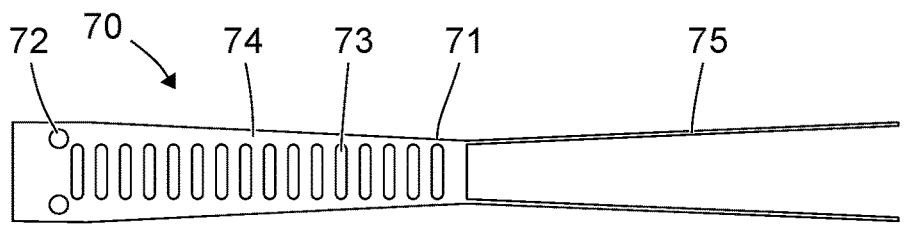
FIG. 4 shows a schematic view of a further first member of an adaptive blade.

FIG. 4 shows a schematic view of a further first member 70 which, in terms of certain features, properties and functions, is similar to the first members shown in FIGS. 1 to 3 for or of adaptive blades. The view shown in FIG. 4 corresponds to that of FIG. 3. Features, properties and functions of the first member 70 that distinguish it from the first members shown in FIGS. 1 to 3 are described below in particular.

The first member 70 shown in FIG. 4 differs from the first members shown in FIGS. 1 to 3 particularly in that the lengths of the recesses 73 measured in a direction orthogonal to the longitudinal direction of the first member 70 are equal. The distances of the ends of the recesses 73 from the longitudinal edges 71 of the first member 70 therefore decrease from the proximal end to the distal end. Correspondingly, the elasticity of the first member 70 increases from the proximal end to the distal end.

Figure 5:
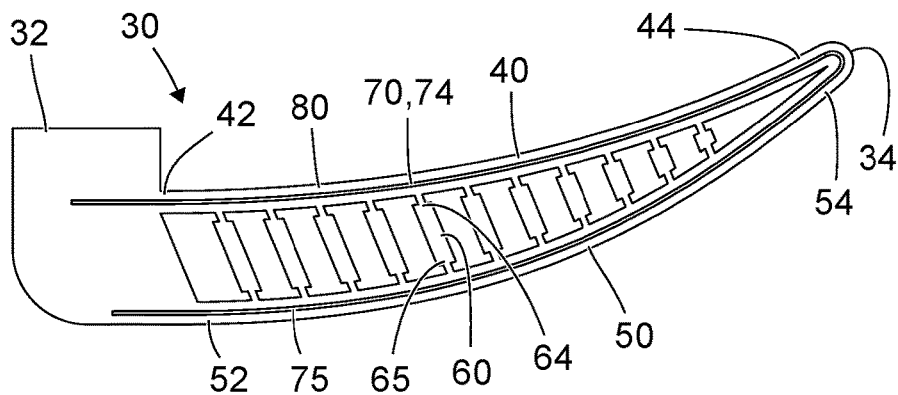
FIG. 5 shows a schematic view of an adaptive blade.

FIG. 5 shows a schematic view of a further adaptive blade 30 which, in terms of certain features, properties and functions, is similar to the adaptive blade shown in FIG. 1. The drawing plane of FIG. 5 is parallel to the longitudinal direction of the adaptive blade 30 and would be parallel to a handle if the latter were connected in the intended manner to the adaptive blade 30.

Figure 6:
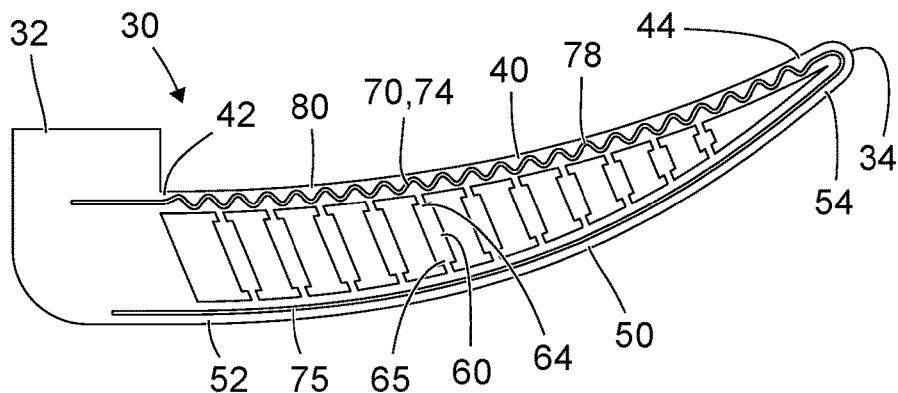
FIG. 6 shows a schematic view of a further adaptive blade.

FIG. 6 shows a schematic view of a further adaptive blade which, in terms of certain features, properties and functions, is similar to the adaptive blades shown in FIGS. 1 and 5. The view in FIG. 6 corresponds to that of FIG. 5. Features, properties and functions that distinguish the adaptive blade 30 shown in FIG. 6 from the adaptive blades shown in FIGS. 1 to 5 are described below in particular.

The adaptive blade shown in FIG. 6 differs from the adaptive blades shown in FIGS. 1 to 5 particularly in that the first member 70 has no recesses, and instead it has waves or corrugations 78. Each individual wave or corrugation 78 extends in a direction orthogonal to the longitudinal direction of the first flexible bar 40 and thus orthogonal to the drawing plane of FIG. 6. The waves or corrugations 78 increase the flexural elasticity of the region 74 of the first member 70 arranged in the first flexible bar 40 (compared to a first member 70 having neither waves/corrugations nor recesses) and therefore the flexural elasticity of the first flexible bar 40 and of the entire adaptive blade 30. At the same time, the waves or corrugations 78 increase the torsional stiffness of the region 74 of the first member 70 arranged in the first flexible bar and therefore also the torsional stiffness of the first bar 40 and of the entire blade 30.

Figure 7:
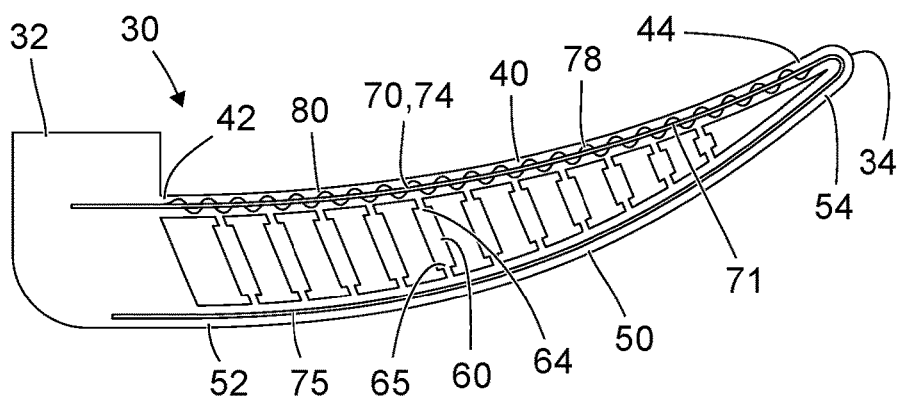
FIG. 7 shows a schematic view of a further adaptive blade.

FIG. 7 shows a schematic view of a further adaptive blade which, in terms of certain features, properties and functions, is similar to the adaptive blades shown in FIGS. 1, 5 and 6. The view in FIG. 7 corresponds to those of FIGS. 5 and 6. Those features, properties and functions of the adaptive blade 30 in FIG. 7 that distinguish it from the adaptive blades shown in FIGS. 1, 5 and 6 are described below in particular.

The adaptive blade 30 shown in FIG. 7 differs from the adaptive blade shown in FIG. 6 particularly in that the waves or corrugations 78 do not reach as far as the longitudinal edges 71 of the first member 70. The longitudinal edges 71 of the first member 70 are therefore likewise smooth and have a likewise continuous curvature, as in the adaptive blades shown in FIGS. 1 to 5.

Figure 8:
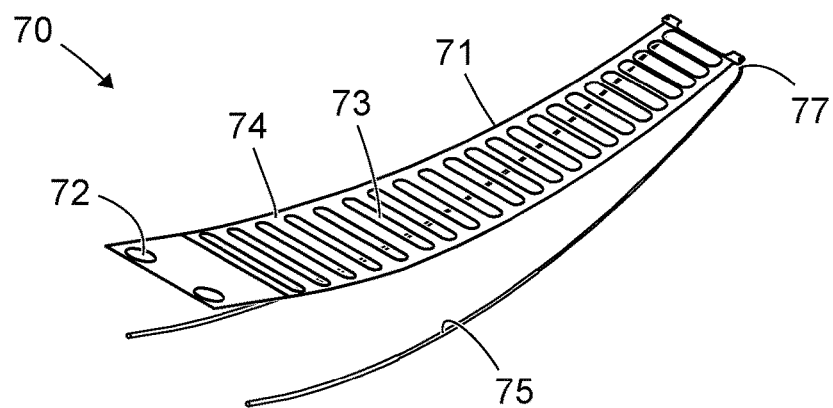
FIG. 8 shows a schematic axonometric view of a further first member of an adaptive blade.

FIG. 8 shows a schematic axonometric view of an alternative embodiment of the first member 70 of the adaptive blade 30 shown in FIG. 1. The viewing direction from which the first member 70 is shown in FIG. 8 corresponds to that of FIGS. 1 and 2, while in other respects the view corresponds to that of FIG. 2. In particular, the first member 70 in FIG. 8 is shown without the casing provided by the second member 80, and it is therefore shown in solid lines.

The member 70 shown in FIG. 8 is similar, in terms of certain features, properties and functions, to the first member shown in FIG. 2. Those features, properties and functions that distinguish the first member 70 shown in FIG. 8 from the first member shown in FIG. 2 are described below in particular.

The first member 70 shown in FIG. 8 differs from the first member shown in FIG. 2 particularly in that it is not formed from a single piece of sheet metal. Rather, the first member 70 comprises a region 74, provided for arrangement in the first flexible bar 40 (cf. FIG. 2), and two regions 75 which are joined to the region 74 and which are provided for arrangement in the second flexible bars 50. The region 74 provided for arrangement in the first flexible bar is similar to that of the first member shown in FIG. 2. Each region 75 provided for arrangement in a second flexible bar has a cross-sectional area decreasing from the proximal end (bottom left in FIG. 8) to the distal end (top right in FIG. 8). The distal ends of the regions 75 provided for arrangement in the second flexible bars are inserted into bores at the distal end of the region 74 provided for arrangement in the first bar and are connected to the region 74, for example, by laser welding.

In the first member 70 shown in FIG. 8, each region 75 provided for arrangement in a second flexible bar has a cross section decreasing in steps from the proximal end to the distal end. The flexural elasticity of each region 75 provided for arrangement in a second flexible bar 50 therefore increases from the proximal end to the distal end.

In particular, each region 75 provided for arrangement in a second flexible bar 50 is produced from a first tube, a second tube thinner and longer than the first tube, and a wire. The second tube is arranged in the first tube and protrudes distally from the latter. The wire is arranged in the second tube and protrudes distally from the latter. The proximal ends of the second tube and of the wire are in particular arranged at a proximal end of the first tube. The cross sections are chosen such that the wire is guided with little play in the second tube and the second tube is guided with little play in the first tube. The first tube, the second tube and the wire can be connected to each other by adhesive bonding, welding or soldering or in some other way.

Alternatively, each region 75 provided for arrangement in a second flexible bar can be produced from one piece of wire whose cross section decreases from the proximal end to the distal end. For example, the cross section of the wire is circular at its proximal end and has the shape of a segment of a circle at its distal end. Proceeding from a wire of circular cross section, such a cross-sectional profile can be generated, for example, by milling along a plane or another surface that is not parallel to the wire. The starting diameter of the wire is 0.8 mm, for example.

The surface and/or the height (measured in the direction of the curvature of the region 75 in the configuration of the first member 70 shown in FIG. 8) of the cross section of each region 75 can vary continuously or discontinuously from the proximal end to the distal end, in order to generate for the region 75 a flexural elasticity that is optimal for the intended use. The surface and/or the height can vary monotonically or strictly monotonically, for example according to an affine-linear equation.

In the first member 70 shown in FIG. 8, the region 74 provided for arrangement in the first flexible bar has recesses 73 which, in shape, size and arrangement, correspond to those of the first member shown in FIG. 2. Alternatively, in a departure from the view in FIG. 8, the region 74 of the first member 70 provided for arrangement in the first flexible bar can have recesses of another size and arrangement (as shown in FIGS. 3 and 4 for example) and/or waves or corrugations (as shown in FIGS. 6 and 7 for example).

Figure 9:
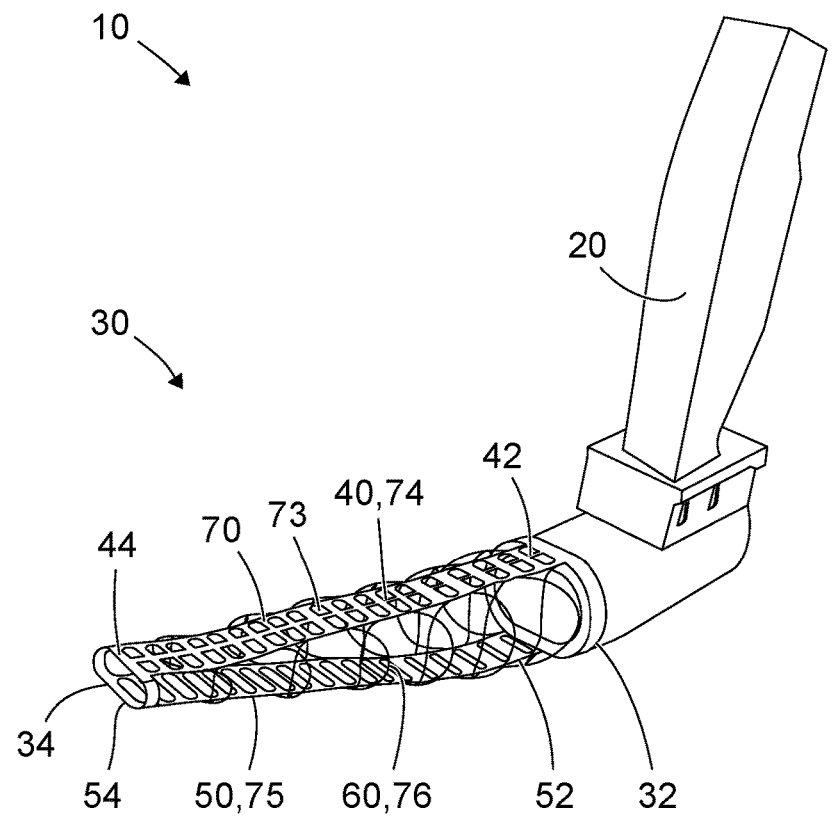
FIG. 9 shows a schematic view of a further intubation laryngoscope.

FIG. 9 shows a schematic axonometric view of a further adaptive intubation laryngoscope 10 which, in terms of certain features, properties and function, is similar to the adaptive intubation laryngoscope shown in FIG. 1, and of which the adaptive blade 30 is similar, in terms of certain features, properties and functions, to the blades shown in FIGS. 1 to 8. Features, properties and functions which distinguish the adaptive blade 30 of the adaptive intubation laryngoscope 10 shown in FIG. 9 differ from the adaptive blades shown in FIG. 9 are described below in particular.

The adaptive blade 9 of the intubation laryngoscope shown in FIG. 9 differs from the adaptive blades shown in FIGS. 1 to 8 particularly in that both a first flexible bar 40 and a second flexible bar 50 are also formed as connecting structures 60 between the flexible bars 40, 50 made from a single tubular member 70. This tubular member 70 has the shape of a conical tube with numerous perforations or recesses. Web-shaped surfaces or regions 74, 75, 76 remaining between the perforations form the first flexible bar 40, the second flexible bar 50 and the connecting structures 60. The first flexible bar 40 is provided in particular to rest on the surface of the tongue of a patient.

In contrast to the adaptive blades shown in FIGS. 1 to 8, only one second flexible bar 50 is provided on a side of the adaptive blade 30 not intended to rest on the tongue of a patient, which flexible bar 50, in the example shown, is however just as wide as the first flexible bar 40. In the same way as in the adaptive blade shown in FIG. 1 and the first members shown in FIGS. 2 to 4 and 8, several recesses 73 are provided in the first flexible bar 40. Accordingly, several recesses are also provided in the second flexible bar 50. The recesses 73 in the flexible bars 40, 50, and in the regions 74, 75 of the tubular member 70 that form the flexible bars 40, 50, influence the flexural elasticity and the torsional stiffness of the tubular member 70 and therefore of the adaptive blade 30.

The torsional stiffness is moreover influenced by the arc-shaped regions 76 of the tubular member 70, which form the adaptive blade 30 and which act as connecting structures 60. The arc-shaped regions intersect each other in pairs at two intersection points.

The proximal end 32 and the distal end 34 of the adaptive blade 30 are each formed by annularly closed regions of the tubular member 70. The elongate cross sections of the tubular member 70 can be seen at the proximal end 32 and at the distal end 34 of the adaptive blade 30. The cross section of the tubular member 70 decreases monotonically from the proximal end 32 to the distal end 34.

In the example shown, the cross sections of the tubular member 70 each have two mutually opposite semicircular portions and, between these, two mutually opposite straight portions.

In a departure from the view in FIG. 9, the tubular member 70 as the first member of the adaptive blade 30 can be enclosed partially or completely by a second member. In this case, the second member, particularly on account of the elastic properties of its material and/or its wall thicknesses and other dimensions, has a greater elasticity than the first member 70, such that the elastic properties of the adaptive blade 30 are mainly or largely determined by the elastic properties of the tubular member 70. The second member can prevent contact between surfaces of the first member 70 and a patient. Sharp edges or inadequate biocompatibility of the material of the tubular member 70 therefore cause no limitations in the use of the adaptive blade 30.

Figure 10:
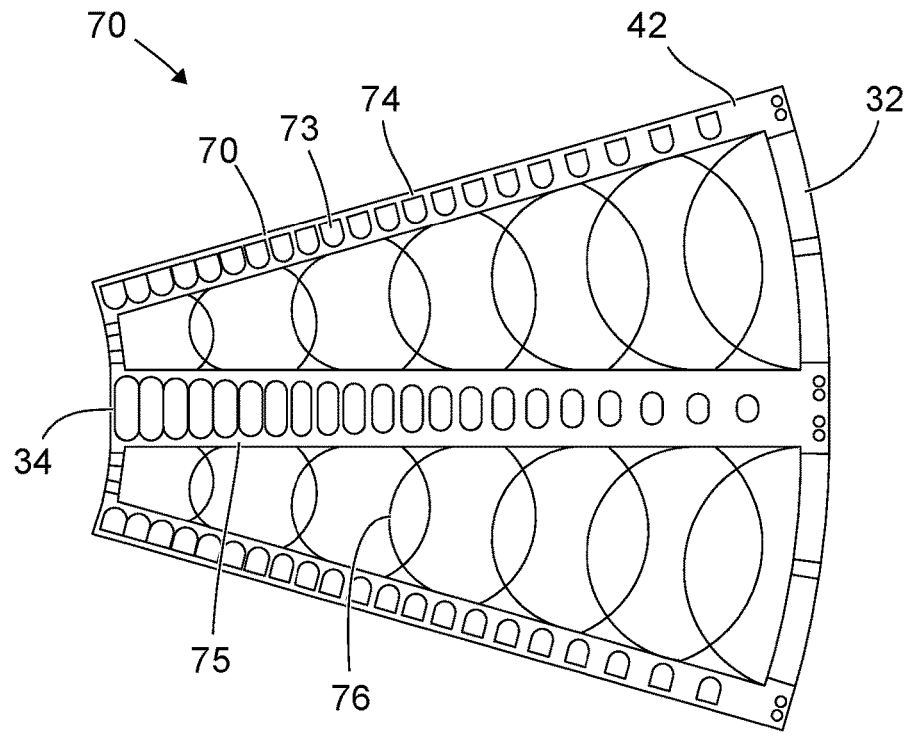
FIG. 10 shows a schematic view of a member of the adaptive blade of the intubation laryngoscope from FIG. 9.

FIG. 10 shows a schematic view of a development of the tubular member 70 of the adaptive blade 30 shown in FIG. 9, and therefore a view of an already cut or punched but as yet unbent metal sheet, from which the tubular member 70 of the adaptive blade 30 shown in FIG. 9 is to be formed.

FIG. 10 clearly shows those regions 76 which form the connecting structures 60 of the adaptive blade 30 (cf. FIG. 9) and which are shaped as arcs of a circle in the development. Two arc-shaped regions 76 curved in mutually opposite directions intersect each other approximately orthogonally at two respective intersection points.

In all of the adaptive blades shown in FIGS. 1 to 10 and in all their variants, the first member or tubular member 70 is formed in particular from a sheet of spring steel, nitinol or another metal, and the second member is formed in particular of an elastomer. Alternatively, the first member 70 can be formed of a fiber-reinforced plastic or another plastic. Particularly in an embodiment similar to the one shown in FIGS. 9 and 10, in which the first member also forms the connecting structure 60, the second member can be omitted. The adaptive blade can be formed as a two-component injection molding.

Elastic properties of the adaptive blades shown in the figures and of their variants, varying from the proximal end to the distal end can be obtained by varying dimensions of several recesses or varying dimensions of waves or corrugations. Alternatively or in addition, elastic properties varying from the proximal end to the distal end can be generated by varying wall thicknesses. This applies particularly when the first member is not produced from a metal sheet but instead by a casting process or by an additive process.

In all of the intubation laryngoscopes shown in the figures, the connection between handle 20 and adaptive blade 30 can be produced by a latching connection. In all of the intubation laryngoscopes shown in the figures, it is possible, in contrast to the views in the figures, to provide a channel for insertion of an endoscope, a light source and/or another instrument. Moreover, in contrast to the views in the figures, a camera, an image transmission device and/or a light source can be integrated in the adaptive blade.

REFERENCE SIGNS 10 intubation laryngoscope
20 handle of the intubation laryngoscope 10
30 adaptive blade of the intubation laryngoscope 10 or for the intubation laryngoscope 10
32 proximal end of the adaptive blade 30
34 distal end of the adaptive blade 30
40 first flexible bar of the adaptive blade 30
42 proximal end of the first flexible bar 40
44 distal end of the first flexible bar 40
50 second flexible bar of the adaptive blade 30
52 proximal end of the second flexible bar 50
54 distal end of the second flexible bar 50
60 connecting structure or strut
64 first end of the connecting structure 60, connected to the first flexible bar 40
65 second end of the connecting structure 60, connected to the second flexible bar 50
70 first member or tubular member or core member
71 longitudinal edge of the first member 70
72 fastening hole in the first member 70
73 recess in the region 74 of the first member 70 for the first flexible bar 40
74 region of the first member 70 arranged in the first flexible bar 40 or forming the first flexible bar 40
75 region of the first member 70 arranged in the second flexible bar 50 or forming the second flexible bar 50
76 arc-shaped region of the first member 70 between the first flexible bar 40 and the second flexible bar 50

77 curved region or bend of the first member 70 at the distal end 34 of the adaptive blade 30
78 wave or corrugation in the first member 70
80 second member

The invention claimed is:

1. An adaptive blade for a laryngoscope, comprising:
a proximal end, which is mechanically connectable or connected to a handle in order to form an adaptive laryngoscope;
a first flexible bar, which extends from the proximal end of the adaptive blade to a distal end thereof;
a second flexible bar, which extends from the proximal end of the adaptive blade to the distal end thereof; and
a connecting structure with a first end, which is connected to the first flexible bar in an articulated manner, and with a second end, which is connected to the second flexible bar in an articulated manner,
wherein the first flexible bar is formed by a first member made of a first material and a second member made of a second material, and
wherein an interface between the first member and the second member extends over at least half a distance between the proximal end and the distal end of the adaptive blade.

2. The adaptive blade according to claim 1, wherein
the first member is a core member, and
the second member is a jacket member in which the first member is at least partially embedded.

3. The adaptive blade according to claim 1, wherein
the first material has a first elastic modulus $E_1$ and the second material has a second elastic modulus $E_2$, wherein the first elastic modulus $E_1$ is greater than the second elastic modulus $E_2$.

4. An adaptive blade for a laryngoscope, comprising:
a proximal end, which is mechanically connectable or connected to a handle in order to form an adaptive laryngoscope;
a first flexible bar, which extends from the proximal end of the adaptive blade to a distal end thereof;
a second flexible bar, which extends from the proximal end of the adaptive blade to the distal end thereof; and
a connecting structure with a first end, which is connected to the first flexible bar in an articulated manner, and with a second end, which is connected to the second flexible bar in an articulated manner,
wherein the first flexible bar is formed by a first member made of a first material and a second member made of a second material,
wherein an interface between the first member and the second member extends over at least half a distance between the proximal end and the distal end of the adaptive blade, and
wherein the first member is formed from a metal sheet or another plate-shaped semi-finished product.

5. The adaptive blade according to claim 1, wherein the first member has a recess.

6. The adaptive blade according to claim 5, wherein
the recess extends orthogonally or substantially orthogonally with respect to a longitudinal direction of the first flexible bar.

7. The adaptive blade according to claim 4, wherein the first member is undulating.

8. The adaptive blade according to claim 1, wherein several recesses, waves or corrugations of the first member have at least either different dimensions or different spacings.

9. The adaptive blade according to claim 1, wherein the first member forms at least a part of the second flexible bar.

10. The adaptive blade according to claim 1, wherein a region of the first member, arranged in the second flexible bar, comprises a tube and a wire partially arranged in the tube, or a wire with a cross section varying from the proximal end to the distal end, or in some other way has a cross section varying from the proximal end to the distal end.

11. The adaptive blade according to claim 1, wherein:
the first flexible bar comprises a third member made from the first material or from a further material, and
the second member is arranged between the first member and the third member.

12. The adaptive blade according to claim 4, wherein the first member has a shape of a multiple perforated tube.

13. The adaptive blade according to claim 12, wherein the first member has a shape of a surface of a generalized cone.

14. The adaptive blade according to claim 12, wherein the first member has
a first region, which is arranged in the first flexible bar,
a second region, which is arranged in the second flexible bar, and
several arc-shaped regions, which connect the first region to the second region and are arranged in several connecting structures of the adaptive blade.

15. An adaptive laryngoscope comprising:
an adaptive blade;
a handle part, which is mechanically connectable or connected to the proximal end of the adaptive blade,
wherein the blade comprises:
a proximal end, which is mechanically connectable or connected to the handle part in order to form the adaptive laryngoscope;
a first flexible bar, which extends from the proximal end of the adaptive blade to a distal end thereof;
a second flexible bar, which extends from the proximal end of the adaptive blade to the distal end thereof; and
a connecting structure with a first end, which is connected to the first flexible bar in an articulated manner, and with a second end, which is connected to the second flexible bar in an articulated manner,
wherein the first flexible bar is formed by a first member made of a first material and a second member made of a second material, and
wherein an interface between the first member and the second member extends over at least half a distance between the proximal end and the distal end of the adaptive blade.

16. The adaptive laryngoscope according to claim 15, wherein the interface comprises a surface along which the first member and the second member directly adjoin each other.

17. The adaptive blade according to claim 4, wherein the interface comprises a surface along which the first member and the second member directly adjoin each other.

18. The adaptive blade according to claim 1, wherein the interface comprises a surface along which the first member and the second member directly adjoin each other.

* * * * *